United States Patent [19]
Alvarez et al.

[11] Patent Number: 5,984,884
[45] Date of Patent: Nov. 16, 1999

[54] CASTING TAPE ARTICLE AND METHOD FOR MOLDING CASTS

[75] Inventors: Jose A. Alvarez, Delray Beach; Roy A. Morris, Plantation, both of Fla.

[73] Assignee: EBI Medical Systems, Inc., Parsippany, N.J.

[21] Appl. No.: 09/040,038

[22] Filed: Mar. 17, 1998

Related U.S. Application Data

[63] Continuation-in-part of application No. 08/841,812, May 5, 1997.

[51] Int. Cl.[6] .......................................................... A61F 5/00
[52] U.S. Cl. .......................... 602/6; 602/6; 602/1; 602/8; 206/440
[58] Field of Search ........................ 602/6, 8, 1; 206/440

[56] References Cited

U.S. PATENT DOCUMENTS

| | | |
|---|---|---|
| 3,062,370 | 11/1962 | Morin . |
| 4,502,479 | 3/1985 | Garwood et al. ........................ 128/90 |
| 5,620,095 | 4/1997 | Delmore et al. ........................ 206/438 |
| 5,738,639 | 4/1998 | Cueman et al. ............................. 602/6 |

*Primary Examiner*—Richard J. Apley
*Assistant Examiner*—Kelvin Hart
*Attorney, Agent, or Firm*—Harness, Dickey & Pierce, P.L.C.

[57] ABSTRACT

The present invention provides a lubricant-impregnated porous substrate. The lubricant-impregnated porous substrate may be used to deliver lubricant as needed to gloves or other surface contacting a tacky resin material during molding or forming of the tacky material. In particular, the lubricant-impregnated porous substrate may be used to lubricate gloves during molding and forming of orthopedic casting materials. The lubricant-impregnated porous substrate may be packaged one or more in a container, and the lubricant-impregnated porous substrate may also be packaged as a kit with the orthopedic casting material. The orthopedic casting material preferably comprises a tape or sheet impregnated with a tacky material wrapped around a core, with the core having multiple projections extending radially outward from a central cylinder to hold the sheet away from the surface of the inner cylinder.

27 Claims, 1 Drawing Sheet

CASTING TAPE ARTICLE AND METHOD FOR MOLDING CASTS

This is a continuation-in-part of U.S. patent application Ser. No. 08/841,812, filed May 5, 1997.

FIELD OF THE INVENTION

The present invention relates to methods and articles for forming orthopedic casts, and optionally the ornamental design as shown in the drawings, and to a method for controlled, on-demand lubricant delivery to gloves or other surfaces, the lubricant providing an outer layer on said gloves or surfaces to allow touching or handling of tacky materials without sticking. The invention also relates generally to methods for molding a water-activated or water-reactive resin impregnated tape or sheet by submerging a roll of tape in water and applying the wet tape by unrolling the tape while at the same time wrapping the tape around an item. In a particularly preferred application, the process provides for applying tacky orthopedic casting materials about a body part to form an orthopedic cast and particularly for on demand lubrication of gloves during handling and molding the casting materials prior to hardening of the casts.

The present invention further relates to a cast kit including at least one flexible substrate impregnated with the lubricant.

The present invention further relates to porous articles that are impregnated with a lubricant and packages including one or more of such articles.

BACKGROUND OF THE INVENTION

In many instances it is necessary or desirable to form or mold tacky materials by hand, generally using protective gloves. For example, tacky resinous materials may be molded by hand into certain forms or shapes. In particular, the tacky materials may be a resin impregnated into a porous substrate. Practical uses of such materials include knitted or woven fiberglass impregnated with a tacky material that may be used to repair water pipes or boats, tacky epoxy materials that may be used in repairing mufflers and automobile bodies, tacky epoxy resin wraps that may be used to repair poles such as utility poles like telephone poles, and the tacky, curable materials that are widely used in making orthopedic casts and splints. In each of these cases a lubricant may be applied to protective gloves to prevent the gloves from sticking to the tacky resinous material.

In forming orthopedic casts and splints, in particular, it has become necessary to devise a simple and versatile means of lubricant delivery to a glove. Casts and splints are widely used for immobilizing a body member, for example to allow a broken bone to heal properly. Plaster of paris casts have recently been largely replaced in many applications by orthopedic bandages or sheets impregnated with tacky synthetic resin mixtures. The synthetic resins used in combination with certain knitted or woven substrates offer a number of advantages over the old plaster of paris materials. Casts made from the synthetic materials are lighter, stronger, harden more quickly, allow for better air circulation, and are not water sensitive.

Among the synthetic resin compositions used to prepare casting materials are water-activated or water-curable synthetic resin compositions and thermoplastic resin compositions. Like the old plaster casting material, the water-activated or water-curable synthetic resin impregnated bandages or sheets, which may also be called tapes, are wetted before application to the body member. The water begins the curing reaction that hardens the cast. Other compositions for casting materials use synthetic resin compositions employing different kinds of curing mechanisms, for example crosslinking through unsaturation.

The synthetic resin orthopedic sheets being used, however, are more difficult to mold about the body member than the old plaster of paris casting sheets due to the tackiness of the resin. This problem may be overcome by interjecting a lubricant between the tacky bandage and the surface, usually a gloved hand, that is being used to mold the cast.

Various means of delivering the lubricant to the glove have been suggested. A mixture of water, sorbitol, mineral oil, and silicone fluid is commercially available from 3M Co., St. Paul, Minn., under the tradename Cast Cream for application to the gloves after wrapping the cast but before molding the cast. Richard et al. disclose a lubricated glove for applying orthopedic cast bandage in EP 712 618. A hydrophilic lubricant is added to a flexible elastic glove material. In U.S. Pat. No. 5,438,709, Green et al. disclose lubricated gloved formed from a elastomer, preferably a latex, with a lubricating polyvinyl alcohol external coating. The PVA may be thickened with, e.g., rhamsan gum. The external coating may be applied by dipping the glove in a solution of the lubricant, followed by drying the coating. In U.S. Pat. No. 5,439,439, Green et al. disclose a similar lubricated glove coated with polyvinylpyrrolidone. These gloves are believed to be difficult to manufacture reproducibly. A further drawback to these coated gloves is that the person molding the cast has no control over the amount of lubricant applied to the gloves.

Another approach that has been used is to "prelubricate" the casting sheet or tape, i.e., to provide a lubricant to a part of the casting sheet that is impregnated with the tacky resin, as opposed to the current method of applying the lubricant to the gloves. Scholz et al. disclose in U.S. Pat. Nos. 4,667,661 and 4,774,937 curable resin-coated sheets prelubricated with a hydrophilic lubricant. The lubricant is present in an amount sufficient to reduce the kinetic coefficient of friction of the sheet surface to less than 1.2. Dull et al., U.S. Pat. No. 4,937,146, impregnate a tape with a mixture of a resin and a non-polar hydrophobic lubricant. The mixture is unstable to the extent that at least part of the lubricant migrates to the surface of the coated sheet to impart low surface tack. Prelubricating all surfaces of the sheets, however, has the drawback that more lubricant is used than is necessary or desirable, and there is no control over the amount or time of application. For instance, it may be desirable to have the wrapped layers stick to one another without slipping and to have the end of the sheet or bandage stick to the surface of the casting sheet wrap in order to terminate the application of the sheet. Moreover, incorporating certain lubricants, such as mineral oil, into the curable resin composition may result in longer set time due to the dilution of the resin curing sites. It is also necessary to avoid a lubricant that would react with the casting resin during storage, as reaction could harden the resin and make the product unusable.

A water-soluble liner layer for casting sheets is disclosed by Scholz et al., WO 94/23769. The liner prevents pooling of resin from out of the casting sheet roll and prevents adhesion of adjacent layers of the roll. The reference discloses that the liner dissolves when the casting sheet is immersed in water to expose the casting sheet. The dissolved liner may also lubricate the casting sheet. This method of lubricating the whole length of the casting sheet, however, is subject to the same shortcomings as the pre-lubricating method. Edenbaum, U.S. Pat. No. 5,476,440 discloses a bandage roll with a permeable core that delivers lubricant. The core has a water permeable base and a lubricant that can be released from the core. After the bandage is applied to a limb to form a cast, the core is wetted and squeezed to release a lubricant that is then applied to the surface of the cast to facilitate molding and smoothing of the cast. While the Edenbaum invention does not appear to lubricate the entire bandage, the lubricant appears to be available only after the bandage has been completely wrapped, with the result that some difficulties may remain in wrapping the tacky bandage before the core with lubricant is reached.

The present invention provides an improved means of delivering a desired amount of lubricant to selected sites on the gloves one or more times when working with tacky materials, in particular tacky resins and polymers, and to articles used in such methods. In one embodiment, the present invention concerns delivering lubricant to gloves during forming an orthopedic cast to prevent the gloves from sticking to the casting material, as well as an orthopedic casting kit for carrying out the method. A lubricant-impregnated porous substrate and a package containing one or more such substrates is also provided.

In addition, the prior cores such as the one provided by the Edenbaum reference do not offer any improvement for the problem of end lay down. Poor end lay down occurs when previously known cores are used because the end of the bandage closest to the core is turned under in order to secure that bandage in place when the roll is being wrapped. When the bandage is then unrolled from the core and wrapped about a limb, the inner end next to the core that was turned becomes the outer end of the orthopedic cast. The edge that was turned to secure the bandage tends not to lie flat, requiring extra care and attention by the casting technician when the cast is smoothed and molded. Thus, the need remains for a method of lubricant delivery that offers more control for the casting technician, and, additionally, for a casting tape article with improved end lay characteristics.

SUMMARY OF THE INVENTION

It has now been discovered that an improved casting tape article can be made by wrapping a tape or sheet impregnated with a tacky material on a core, with the core having multiple projections extending radially outwardly from a central cylinder. The projections hold the tape or sheet away from the surface of the inner cylinder of the core, at least in part. The core of the invention allows water to easily reach water-reactive or water-activated curable resins that are used as the tacky material of the casting tape, particularly in the inner regions of the roll. In addition, the leading end for wrapping can be placed between adjacent projections, with the result that the tape can be rolled without folding or bending the end in a way that would cause poor end lay down during use.

The invention also provides an article as described that further includes a lubricant impregnated porous substrate, particularly a sheet or towelette, that covers at least a part of the outer circumference of the roll of casting tape, and preferably is wrapped around the circumference of the roll of casting tape. In addition, there may be a barrier layer between the lubricant impregnated porous substrate and the roll of casting tape that would prevent any significant migration of lubricant into the casting tape or tacky resin. For instance, the lubricant impregnated porous sheet or towelette may have a backing or laminate layer on one side through which the lubricant cannot readily migrate, the laminate or backing side of the sheet being placed next to the casting tape to slow or prevent migration of lubricant to the roll of casting tape during storage. The present invention also provides an orthopedic casting kit containing the casting tape article.

In one method of the present invention, a porous substrate is impregnated with a lubricant. The impregnated substrate is then used to deliver lubricant to the gloves of the person forming the tacky resin or cast material to prevent the gloves from sticking to the resin material or cast tape during application and molding of the material. The present method offers a number of advantages over prior methods. First, only as much lubricant as is necessary is applied to the gloves and the cast being molded. Accordingly, a certain amount of tackiness may be maintained if desirable. Secondly, because the lubricant is not admixed with the curable composition, or applied to the cast sheet or tape for the purpose of significantly affecting its tackiness, the lubricant may be selected from a wide variety of materials, including materials that might be reactive toward the curable composition of the casting sheet or other tacky material being formed, or that would otherwise affect shelf life or performance. In addition, the lubricant may be reapplied to the gloves as desired during application and molding of the cast material, or while working with other tacky materials. Thus, the level of tackiness can be controlled according to the preference of the individual casting technician. Finally, the lubricant need not be hydrophilic, as is required in many of the prior methods described above.

The present invention does not suffer from the end lay-down problem of previous designs in which it way necessary to create an overlap of the casting sheet or tape on the flat surface of the core. It is an advantage both for ease of manufacture and for performance of the casting tape that no overlap is needed in wrapping the tape around the core of the present invention. The novel cores also improve delivery of water to inner layers of the casting tape for when the casting tape is impregnated with a water-activated resin. The improved delivery of water may result in a stronger cast after curing of the resin.

DETAILED DESCRIPTION

The invention provides an article that is a porous substrate impregnated with a lubricant. The impregnated substrate is used to lubricate gloves before handling tacky materials, such as tacky resin or polymer compositions, so that the tacky materials may be worked with and formed without having the gloves, or other surface used for the handling, stick to the tacky material. It is our intention for the scope of the invention to include in its methods and combinations all tacky materials, while herein after the description may focus on orthopedic casting materials.

Figures 1, 2:
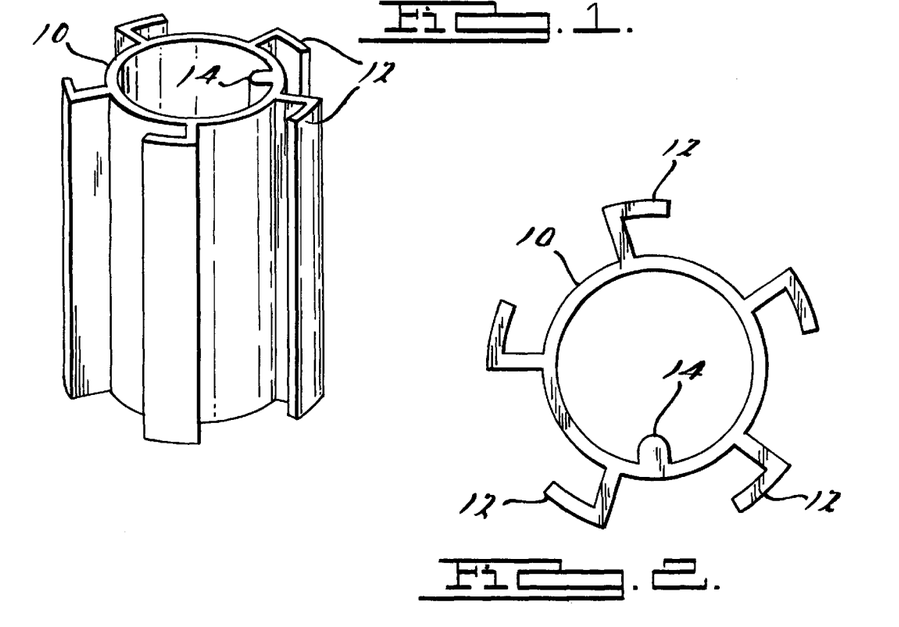
FIG. 1 is a perspective view of a preferred embodiment of a core for a roll of casting tape.
FIG. 2 is a cross-sectional view showing the first preferred embodiment of the core of the present invention.
Figure 3:
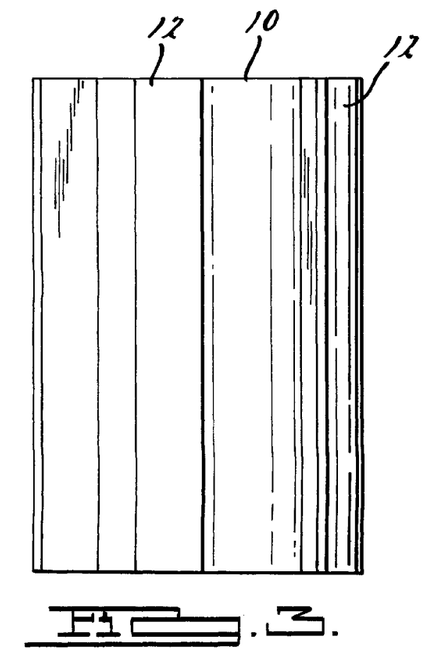
FIG. 3 is a side plan view of the core in the position of FIG. 1, showing three of the radially extending projections.
Figure 4:
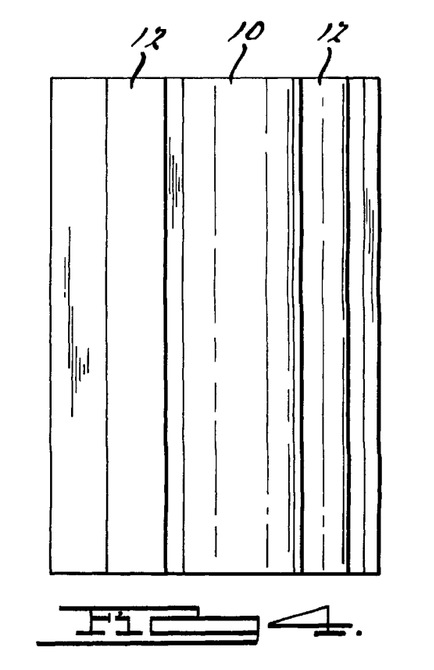
FIG. 4 is a side plan view of the core rotated to show four of the radially extending projections.

The invention further provides a novel core for a roll of a tacky resin or polymer impregnated tape or sheet, particularly for a tacky resin that is water-activated or water-reactive. Referring now to FIG. 1, the core has multiple projections extending radially outward from the surface of the inner core cylinder that hold the tape or sheet away from the surface of the inner core cylinder. The roll with the core of the invention may further include a porous substrate impregnated with a lubricant. The impregnated substrate is used to lubricate gloves before handling the tacky resin impregnated tape or sheet, so that the tacky materials may be worked with and formed without having the gloves, or other surface used for the handling, stick to the tacky material. It is our intention for the scope of the invention to include in its methods and combinations all tacky materials, while herein after the description may focus on orthopedic casting materials.

The lubricant impregnated porous substrate is contacted with the surface of the glove, for example by rubbing the lubricant impregnated porous substrate on the desired surface of the glove, to deliver lubricant to the glove one or more times. One or both of the lubricant impregnated porous substrate or gloves may optionally be wetted with water or immersed in water before transferring the lubricant to the glove, and this step may be preferred when the lubricant is water soluble or water dispersible. In some cases, the lubricant impregnated substrate may be immersed in water or wetted before being used one or more times to deliver lubricant as needed to the gloves.

The porous substrate that is impregnated with a lubricant should be capable of delivering the lubricant to the desired surfaces, preferably in a controlled fashion. Preferably, the porous substrate has at least some flexibility or deformability that aids in lubricant delivery. It is particularly preferred for the porous substrate impregnated with lubricant to be a film, a foam, or a sponge; or a textile or fabric article, including articles that may be described as cloths, sheets, tapes, towelettes, pads, or the like. In a more preferred embodiment, the porous substrate is a cloth, sheet, towelette, pad, or sponge.

In a preferred embodiment, the porous substrate is a towelette, piece of fabric, or similar thin article with holes or pores to hold, and then release, the lubricant. The porous substrate may have a broad range of sizes, but it is preferred to have the porous substrate be of a size that is large enough to deliver a sufficient amount of lubricant but small enough to be easily handled. For example, the porous substrate may have dimensions of a thickness of from about 0.2 millimeter to about 10 centimeters, a length of from about 1 centimeter to about one meter, and a width of from about 1 centimeter to about one meter. Preferred dimensions in the case of a sheet or towelette are thicknesses of up to about 3 centimeters, preferably thickness of less than 2.5 cm, particularly from about 0.02 to about 1.5 centimeters; lengths of up to about 100 centimeters, particularly from about 5 to about 50 centimeters; and widths of up to about 100 centimeters, particularly from about 5 centimeters to about 50 centimeters. It will be appreciated by the skilled artisan that the physical dimensions of the porous substrate will depend upon its nature and the particular application. In another embodiment, the porous substrate is in the form of a continuous web of sheets connected in end-to-end relationship separated by a scored line or perforations, much like paper toweling.

The porous substrate preferably comprises a knitted, woven, or nonwoven textile or fabric. The weight of the fabric is not particularly critical, and may range, for example, from about 1 ounce per square yard to about 15 ounces per square yard. Suitable materials include, without limitation, cotton fabric or cotton felt, ramie, jute, silk, wool, linen, rayon, acetate, triacetate, polyamides such as nylons, acrylics, polyester brushed tricot, and copolymers such as spandex (a polyester-polyurethane), as well as blends of these. Among preferred fabrics are 100% polyester brushed tricot and non-cellulosic paper. Other suitable articles include, without limitation, natural and synthetic sponges, gauze pads of natural or synthetic fibers, and pads filled with absorbent fibers, yarns, or other materials such as cotton, dacron, or fiberfill, preferably those pads having surfaces non-reactive toward the water-curable resin. The porous substrate is preferably strong enough to be handled in and out of water, as for example during the formation of the orthopedic cast, without excessive tearing or disintegration.

The porous substrate is impregnated with at least one lubricating material. The amount of lubricant that is impregnated into the porous substrate is at least about 20%, preferably at least about 50%, more preferably at least about 100%, and still more preferably at least about 400% by weight, based on the weight of the porous substrate. The lubricant-impregnated porous substrate article of the present invention is at least about 16% by weight lubricant, preferably at least about 33% by weight lubricant, more preferably at least about 50% by weight lubricant, and still more preferably at least about 80% by weight lubricant, based on the weight of the article.

The lubricant that is used to impregnate the porous substrate may be selected from a wide variety of lubricating materials. The lubricant is either not reactive with the tacky resin or casting material or else the impregnated porous substrate is separated from the casting sheet during storage in order to prevent any reaction with the resin of the casting sheet. It is also desirable to prevent migration of the lubricant into the curable resin impregnated casting sheet or tape. One means of preventing such contact or migration is by a barrier layer interposed between the lubricant impregnated porous substrate and the curable resin impregnated casting sheet in a casting kit containing both items.

Examples of useful barrier layers include, without limitation, a barrier layer laminated to the lubricant impregnated porous substrate, a barrier layer wrapped between the roll of resin impregnated casting sheet and the lubricant impregnated porous substrate, a combination of lubricant impregnated porous substrate and barrier layer rolled up with the resin impregnated casting sheet on the core, and a barrier layer not attached to either the roll or the lubricant impregnated porous substrate that separates the roll of casting sheet from the lubricant impregnated substrate into different compartments of a cast kit, in each case the barrier layer being of a material that is essentially impervious to the lubricant. Examples of materials suitable for the barrier layer include, without limitation, plastics such as polyolefin materials, especially ethylene and propylene homopolymers and copolymers, polyurethane materials, and other such plastics. When the barrier layer is to be wrapped around the casting tape roll, and particularly when the barrier layer is a layer laminated onto the porous substrate impregnated with the lubricant, it is desirable that the barrier layer have sufficient flexibility so that it can shaped around the roll during manufacture and removed and handled during use without great effort. Preferably, the barrier layer is less than about 10 mils thick, more preferably less than about 5 mils thick, and even more preferably less than about 3 mils thick. Also preferably, the barrier layer is at least about 1 mil thick. A preferred range of thickness for the barrier layer is from about 1 mil to about 5 mils, and even more preferably from about 2 mils to about 3 mils. In a particularly preferred embodiment, the barrier layer is a layer of low density polyethylene laminated to one face of the porous substrate that is impregnated with the lubricant.

Even when there is no barrier layer between the lubricant impregnated material and the curable-resin coated sheet, the lubricant is preferably not deposited onto the surface of the casting material in any appreciable amount or for any appreciable length during storage or at any point prior to use, and the tackiness of the cast sheet preferably remains essentially unchanged in the packaged article.

Examples of useful lubricants include, without limitation, water soluble or hydrophilic polymers such as polyethylene oxide, polyethylene oxide block copolymers such as copolymers of ethylene oxide and propylene oxide, polyvinyl alcohol, hydroxyethyl cellulose, carboxymethyl cellulose, acrylamide-based polymers, and polyvinylpyrrolidone; surfactants such as polyethoxylated fatty alcohols and their salts, including sodium laureth sulfate ethoxylate; fatty amides; fatty acids and their salts, such as metallic or organic stearates; lecithin-based lubricants; waxes, such as carnuba wax and paraffin; sulfonated or carboxylated polymers, such as sulfonated or carboxylated polyurethanes; hydrophilic, oligomeric diols, such as the reaction product of polyethylene oxide glycol with dimethyl sodium sulfoisophthalate in a 2:1 molar ratio; hydrophobic lubricants and oils, such as mineral oils, petrolatum, vegetable oils, and derivatives thereof; synthetic and natural motor oils; silicones and other fluids, oils, and greases, such as polydimethylsiloxanes, polymethylphenylsiloxanes, and polydiphenylsiloxanes, especially those having viscosities of between about 100 and 100,000 centistokes; fluorinated greases, and mixtures of any of these materials. Mixtures may also be employed. In a preferred embodiment, the lubricant is a mixture of an oil and a surfactant. Silicone oils or mixtures of silicone oils and surfactants are particularly preferred. The silicone oil may be up to about 100% by weight, preferably from about 80 to about 100% by weight, and more preferably from about 90 to about 99% by weight of the mixture.

The impregnating lubricant mixture may include other ingredients, such as stabilizers, thickening agents, pigments or colorants, dyes, organic solvents or cosolvents, and so on.

The lubricant impregnated porous articles with the tape or sheet impregnated with a tacky material wound on the core of the present invention, or may be packaged separately, with one or more article per package or container, for storage before use. The invention further provides a container comprising one or more of the lubricant-impregnated porous substrates. In the case of a volatile lubricant, the container may comprise a closed or, preferably, sealed package capable of preventing evaporation of the lubricant, wherein the package contains one or more of the lubricant-impregnated porous substrate or substrates.

Packaging suitable for containing lubricant impregnated sheets, towelettes, pads, rolls, sponges, and so on are known. For example, a package dispenser for dispensing sheets or towelettes of the invention may comprise a container, said container having a cavity, and said cavity having therein a plurality of the sheets or towelettes. The container may have an opening on one end through which said sheets or towelettes may be taken or pulled. The container may have one or more leakproof layers, such as a hermetic seal. The seal may be made of a flexible material or of a deformable plastic coated foil or uncoated foil. The container may be made of either a rigid or a flexible material, or a combination of rigid and flexible materials. For example, the container may be formed from a rigid plastic or semi-rigid plastic such as a polyethylene, polypropylene, polyethylene terephthalate, or from a more flexible material such as a composite film.

Multiple articles of the invention may be placed within the container in random or ordered configurations. Thus, in the case of pads or sponges, the articles may be packed randomly in whatever number the cavity allows, while sheets, towelettes, or similar articles may be ordered in stacks or rolls in the containers.

The container may contain, for example, a continuous web of material in compacted form having sheets connected in end-to-end relationship separated by scored lines or perforations, from which the respective sheets can be readily dispensed, one at a time. Such a container may include a body containing the continuous web; a closure for the container; and a dispensing opening through which the web is withdrawn and a sheet of the web separated at the scored line or perforations. Preferably, as each sheet is pulled out and separated, the next sheet is exposed above the dispensing opening. The web may be in the form of a roll, and the web may be drawn for dispensing from the center of the roll. Alternatively, the sheets or towelettes may be stacked face-to-face in the container. In yet another embodiment, the sheets or towelettes may be partially overlapped or stacked as an interfolded array so that when one is withdrawn from the container, the next in the stack is presented in a graspable position.

In general, containers or packages of the kind commercially available for dispensing tissues, paper, towelettes, and similar items can be used a package for the lubricant impregnated porous substrates of the invention having similar shapes or dimensions.

Generally, the lubricant-impregnated porous substrate of the invention is used to apply lubricant to gloves. Suitable gloves that may be used to handle the tacky material include gloves made from polyvinyl chloride, vinyl, latex, butyl rubber, or other such elastomeric materials. The gloves should be substantially nonporous to the lubricant so that the lubricant is not absorbed by the glove but instead remains, at least for the most part, on the surface of the glove.

In one preferred embodiment, the lubricant-impregnated porous substrate is used with a curable-resin impregnated sheet. The curable resin may be any of the kind known in the art, including water-curable, UV-curable, EB-curable, heat-setting, and air-dry (oxygen-curing) materials. In a particularly preferred embodiment, the curable-resin impregnated sheet is an orthopedic casting or splinting material or tape, preferably impregnated with a water-curable resin. Water-curable resins include water-reactive and water-activated resins. An orthopedic cast is formed by transferring lubricant from a lubricant-impregnated porous substrate to a glove on the hand of the person forming the cast. The lubricated glove is used to apply and form a casting material around a body member. Lubricant may be reapplied to the glove as desired during the application and forming of the cast. Water-curable resin impregnated cast sheets or tapes are wetted with water, preferably by immersing the whole roll in water, before forming the cast. The water soaks into the roll of casting tape, facilitated by the gaps provided between the tape and the center cylinder of the core. After the casting material has been applied, it is allowed to harden to form an orthopedic cast around the body member.

The utility of the of lubricant-impregnated article of the invention does not depend upon the curing mechanism of the tacky material, although the particular lubricant may be chosen with the character of the tacky material in mind. For instance, hydroxyl-functional lubricants may be avoided if the tacky material is reactive with hydroxyl groups. In one preferred embodiment, the tacky material is a casting sheet or tape impregnated with a water-activated curable composition. The curable composition comprises, for example, a polymerizable or crosslinking material and may in addition comprise a catalyst or initiator for promoting the desired reaction.

The sheet substrate that is impregnated with the curable resin is preferably an open-weave structure of a fibrous material. Examples of suitable porous material for the casting sheet include, without limitation, woven, knit, and non-woven fabrics of natural and/or synthetic fibers. In a preferred embodiment, the casting material comprises knit fiberglass fabrics, polyester fabrics, acrylic fabrics, or extensible materials such as are described in U.S. Pat. Nos. 4,609,578 and 4,668,563, both of which are incorporated herein by reference. Useful fiberglass-based materials include, without limitation, those disclosed in U.S. Pat. Nos. 4,323,061; 3,686,725; 3,787,272; 3,882,857; 4,376,438; and 4,411,262, the disclosure of each being incorporated herein by reference. A preferred embodiment employs a knitted fabric that combines a high modulus fiber, such as a fiberglass, polyaramide, or polyethylene fiber, with an elastomeric, highly extensible fiber, such as a natural rubber, spandex (a polyurethane), polyisoprene, polybutadiene, diene copolymers, acrylonitrile copolymers, EPM, or EPDM fiber. Casts using substrates that are extensible may be easier to conform to the body of the patient.

The substrate sheet material may be coated with a substance for modifying the fibers of the substrate prior to impregnation with the curable resin mixture. If used, the modifying substance preferably does not interfere with the impregnation or detrimentally affect the performance of the curable resin mixture. One example of a modifying substance is a low modulus binder that may be applied to prevent or reduce fraying of cut ends of the substrate, as is disclosed in U.S. Pat. No. 4,800,872, incorporated herein by reference.

The casting tape, when impregnated with the curable resin, preferably has at least some flexibility. The impregnated casting material should have sufficient flexibility so that it can be molded about a limb without excessive pressure to form need to support and/or protect the limb. The casting material is at least partially impregnated with a curable resin.

The curable resin of the casting material may be any curable resin that satisfies the functional requirements of an orthopedic cast. The resin-impregnated sheet should be pliable before cure, but should upon cure become rigid and strong to support the loads and stresses to which the cast may be subjected by the activities of the patient. The hardening should take place fairly rapidly once curing has been initiated, preferably attaining weight-bearing strength within about 30 minutes. The curable resin is selected from materials that preferably do not emit significant amounts of toxic by-products during curing that might be harmful to either the patient or the person applying the cast. The curable resin also is preferably non-irritating to the skin and should not generate an excessive amount of heat during curing that might cause discomfort or burns to the underlying skin.

The curable resin may cure by a variety of mechanisms. The cure reaction should not generate an amount of heat that would cause discomfort or burns to exposed skin. Among known curable resin systems used for casts are catalyzed polyurethane prepolymers and water-reactive alkoxysilane terminated resins.

The curable resin is preferably a polyurethane prepolymer. Useful polyurethane prepolymers are described, for example, in U.S. Pat. Nos. 4,131,114; 4,411,262; and 4,502,479, each of which are incorporated herein by reference. The polyurethane prepolymer may be prepared by reacting one or more polyisocyanates with one or more polyols in an equivalent ratio of from about 2:1 to about 12:1, and preferably from about 3:1 to about 5:1 isocyanate groups to hydroxyl groups. The polyisocyanate may be aliphatic, cycloaliphatic, or aromatic diisocyanates, triisocyanates, or tetraisocyanates, as well as biurets, isocyanurates, and similar oligomers of these. Examples of useful polyisocyanates include, without limitation, toluene diisocyanates (TDI), including the 2,4 and 2,6 isomers and mixtures of these isomers; diphenylmethane diusocyanates (MDI), including the 4,4', 2,4', and 2,2' isomers and mixtures of these isomers; hydrogenated diphenylmethane diisocyanates, aromatic polyisocyanates derived from phosgenation of the condensation product of aniline and formaldehyde (polymeric MDI), hexamethylene diisocyanate, isophorone diisocyanate, octamethylene diisocyanate, trimethylhexane diisocyanates, dodecamethylene diisocyanates, cyclopentane diisocyanate, cyclohexane diisocyanate, tetramethylxylene diisocyanate, and biurets, allophonates, isocyanurates, and substituted derivatives of these, such as carbodiimide-containing polyisocyanates. Preferred among these are polymeric diphenylmethane diisocyanates (polymeric MDIs).

The polyisocyanate is reacted with at least one polyol. Examples of suitable polyols include, without limitation, polyether polyols, polyester polyols including polycaprolactone polyols, and monomeric diols and triols such as 1,6-hexanediol. Preferred polyols include polyethylene oxide and polypropylene oxide diols and triols, polytetramethylene ether glycols, especially those having a molecular weight of from about 400 to about 2000. Polyalkylene oxide polyols are available commercially, for example from BASF Corporation under the tradename Pluracol® and from Union Carbide Corporation under the tradenames Carbowax® and Polyox®.

The prepolymer is preferably mixed with a catalyst. Preferred catalysts include tertiary amine catalysts such as tertiary alkanolamines, for example dimethylethanolamine and dimethylaminodiethyl ether; 2,2'-dimorpholinodialkylethers such as 2,2'-dimorpholinodiethylether (DMDEE), available commercially from Texaco, Inc., as Thancat DMDEE; and 2,2'-dimorpholinyldialkylethers, such as 4-[2-[methyl-2-(4-morpholinyl)ethoxy]-ethyl]morpholine (MEMPE). The catalyst is preferably included in amounts of from about 0.1% to about 10% by weight of the impregnating resin mixture.

The curable resin mixture preferably has a viscosity that is low enough to allow the mixture to enter the pores of the substrate to produce a resin-impregnated substrate, while the viscosity is high enough that a sufficient amount remains in the substrate so that upon cure the substrate is effectively hardened and good properties are obtained. The viscosity may be modified according to a variety of obvious means, such as by addition of low viscosity materials including, without limitation, organic solvents to reduce viscosity or by addition of thickening agents to increase viscosity. The optimum viscosity may be determined by straightforward testing. In a preferred embodiment of the invention, the viscosity of the curable resin mixture is from about 5000 to about 100,000 centipoise.

The impregnating resin mixture may include other ingredients, such as stabilizers, thickening agents, antifoam agents, pigments or colorants, and so on. Such other additives may be included in minor amounts. The lubricant impregnated porous substrate is substantially free of materials that would interfere with the properties of the lubricant impregnated porous substrate as described herein or that would impair the ability of the lubricant impregnated porous substrate to operate as desired in the methods of the present invention.

The substrate is impregnated with the curable resin mixture. When a casting substrate is impregnated with curable resin mixture, the weight of the curable resin mixture that is impregnated into the substrate is preferably from about 30 to about 125% by weight of the substrate. Generally, the resin mixture may flow into the capillary spaces between fibers of the fabric.

The resin impregnated cast sheet or tape is rolled around a core. In a method of forming an orthopedic cast on a limb, the cast sheet is unwound from the core and applied to the limb to form a cast. The core is made of a material that is sufficiently rigid to adequately support the casting tape or sheet during storage and use. When the tacky resin is water-activated, it is preferred for the core to have at least some flexibility that will allow it to be flexed and squeezed when the tape is placed in the water just prior to forming a cast in order to facilitate absorption of water into the tape. Among preferred classes of plastic materials for the core are polyolefin homopolymers and copolymers, particularly homopolymers or copolymers of ethylene or propylene, and polyurethanes. Particularly preferred are ethylene homopolymers and copolymers, especially low density polyethylene.

Referring to FIG. 2, the core has multiple projections 12 extending radially outwardly from an inner cylinder 10. The projections 12 hold the bandage away from, at least partly, the surface of the inner cylinder 10. Preferably, the core has at least two projections, and more preferably at least three projections. Preferably, the core has up to about 10 projections, more preferably up to about 8 projections, and yet more preferably up to about 6 projections. The projections may in principle have any space around the inner cylinder, but preferably the projections are evenly spaced about the circumference of the cylinder. For example, the projections about a core may be spaced so that the arc from the leading edge from one projection to the leading edge of the next projection will be about 120° when there are three projections, about 90° when there are four projections, about 72° when there are five projections, about 60° when there are six projections, and so on. Even spacing of the projections is not critical, however, and uneven spacing may be employed so long as a sufficient amount of gap between the core and the casting tape when the tape is rolled over the projections to allow easy water intake. The better water saturation obtained using the core of the invention results in increased strength of the final cast after fully curing.

The projections may have a tapering shape with a wider end and narrowing closer to the inner cylinder of the core to help hold the tape away from the inner cylinder. The projections may also have a thickened or flattened end that keeps the casting tape from settling to the base of the projection. Preferably, the projections are L-shaped, as shown in FIGS. 1 and 2, or T-shaped. There is preferably at least some space between the edges of one projection and the next so that the end of the tape or sheet can be easily inserted between any two adjacent projections. The tape or sheet may be inserted under an end of one of the projections to secure the end when rolling is started. In forming the casting tape roll by this method, the end is not folded over or otherwise distorted in a way that would tend to prevent the end from lying flat when the tape is wrapped during use. Rather, the end lies flat after wrapping.

The inner cylinder 10 is hollow and may have a circular or oval cross-section, preferably a circular cross-section. The inner cylinder is hollow to allow the core to be slipped over a spindle for easy winding of the casting tape about the core. The core has an inwardly extending protuberance 14 for engaging the spindle during the winding operation when the casting tape or sheet is wound on the core. In general, the core will have a uniform cross-section along its width so that the cross-sectional dimensions of one end of the core will be symmetrically identical to the cross-sectional dimensions of the other end of the core.

The core is preferably about as long as, or slightly longer than, the casting tape wrapped around it. Typically, orthopedic casting tapes are manufactured in widths of 2, 3, 4, and 5 inches. Preferably, the core is up to about one-quarter inch longer than the width of the casting tape.

The core preferably has a total diameter, particularly for orthopedic casting applications, of at least about one-half inch. "Total diameter" is used to denote the diameter of the circle, or the widest diameter of the oval, defined by the outermost points of the protrusions. It is also preferred that the core have a total diameter of two inches or less. In one preferred embodiment, the total diameter of the core is about 1¼ inches or less, and in a particularly preferred embodiment is about three-quarters of an inch or within about one quarter inch of three-quarters of an inch.

The core may be manufactured according to methods known in the art, such as by blow molding, extrusion, or injection molding.

The invention provides a kit comprising both the lubricant impregnated porous substrate and the resin impregnated cast sheet. The invention also provides a kit comprising both the lubricant-impregnated porous substrate and the roll of resin impregnated cast sheet wound around the core of the invention. When the cast material is a thermoplastic, water-curable, or air-drying formulation, it is preferred for the cast sheet to be sealed in a compartment of the kit. The lubricant-impregnated substrate may be sealed in the same compartment as the cast sheet or may be provided in a different sealed compartment, or (if the lubricant is not volatile) an unsealed compartment of the same kit. In a preferred embodiment, the lubricant is impregnated in a towelette, and the towelette is packaged around the outside circumference of a roll of the cast sheet, the towelette-encompassed roll being sealed inside of a compartment of the kit. It is preferred for the roll and towelette to be separated by a barrier layer. In a preferred embodiment the towelette is polyester tricot laminated on one side with a layer of low density polyethylene. In another preferred embodiment, the lubricant-impregnated sheet and the cast sheet being folded into a single roll, the roll being then sealed inside of a compartment of the kit. In yet a further embodiment of the invention, the lubricant-impregnated sheet and the cast sheet are separated by a third layer that is a barrier layer, such as a polyolefin film, all three layers being folded into a single roll and the roll being then sealed inside of a compartment of the kit. In still a further embodiment of the invention, a lubricant-impregnated porous substrate is placed, and optionally sealed, in one compartment of the kit and the cast sheet is sealed inside of a second, separate compartment of the kit, the two compartments being separated by a barrier layer impervious to the lubricant. This final embodiment is particularly preferred when the lubricant-impregnated porous substrate is a sponge, pad, or other object of a thickness significantly thicker than the thickness of the cast sheet.

Before rolling, the ends of the cast sheet or tape are preferably sealed with heat, providing reinforced ends of about ¼ inch each. The cast sheet is then rolled on the core of the invention by placing the core on a spindle, with the inward protuberance catching on the spindle during turning. One end of the sheet is inserted into a gap between adjacent projections of the core and catches when the core begins to rotate. The core is rotated by the spindle until the entire length of cast tape or sheet is wound on the core.

The cast sheet or tape that is rolled into the roll of the kit may be from about 3.5 to about 4.2 yards, preferably from about 4 to about 4.2 yards in length and from about 1 to about 10 inches, preferably from about 1 to about 5 inches, in width.

The sealing compartments may comprise a peelable layer over a shell of a material inert toward both the lubricant-impregnated substrate and the water-curable resin-impregnated cast sheet. Alternatively, the kit may comprise foil, foil-lined, plastic, or metallized plastic pouches or compartments. The kit may further include gloves suitable for wearing during the cast molding process.

An important aspect of many of the preferred embodiments of the present invention is the ability of the person applying the casting material to control the amount of lubricant applied to the gloves during molding of the cast, as well as the timing of the application. The lubricant may be reapplied to the gloves by wiping the gloves with the wet towelette during forming of the cast and the molding process as necessary.

The roll may be submerged in water along with the towelette or other lubricant-impregnated substrate and squeezed or pressed to enhance water take-up. When the towelette covers the roll, the towelette may be squeezed along with the roll to deliver lubricant to the gloves. Using gloves to which the lubricant has been applied by means of the lubricant-impregnated substrate, the wetted casting tape or sheet is wrapped about the patient's limb, or otherwise applied in multiple adjacent layers The application is assisted by the reduction in tackiness of the substrate relative to the gloves without reducing significantly the tackiness of the cast substrate relative to itself. If the gloves begin to stick to the cast tape, the wetted sheet, sponge, or pad can be picked up and worked between the gloves in order to deposit additional lubricant onto the glove surfaces. When the desired amount casting material has been wrapped around the body member, it is often desirable to further mold the wrapped cast material about the body member. Lubricant may be re-applied from the lubricant-impregnated porous substrate to the gloves before and during molding the wrapped cast material as desired.

It is also sometimes desirable to use less lubricant prior to and during application of the casting material, so that the tape and packaging can be easily handled during the wrapping step. Lubricant, or additional lubricant, can then be employed during the molding step.

After application of the casting material is completed, the casting material is allowed to fully harden to form a cast about the wrapped limb. In one embodiment of the invention, the casting material comprises a thermoplastic composition that hardens on cooling. In a preferred embodiment of the invention, the casting material comprises a curable composition-impregnated sheet, particularly a water-reactive or water-activated curable composition. In the case of a water-reactive or water-activated curable composition, the casting material is immersed in water or otherwise wetted with water prior to applying the casting material around the body member. After the casting material is applied, preferably by wrapping and molding about the body member, the curable composition is cured to form the finished cast.

The invention is illustrated by the following examples, and the ornamental design as shown in FIGS. 1–4. The examples are merely illustrative and do not in any way limit the scope of the invention as described and claimed. All parts are parts by weight unless otherwise noted.

EXAMPLES

Example 1

Preparation of an Orthopedic Casting Kit

A substrate casting sheet of fiberglass with approximately 10% polypropylene fiber, about 3 inches wide and 4 yards long, having approximately 25% stretch, is impregnated with the following mixture:

58 parts by weight Isonate™ 2143L (a diphenylmethane diisocyanate resin available from Dow Chemical, Midland, Mich.), 38 parts by weight PPG 725 (a polypropylene glycol available from Arco Chemical Co., Charlotte, N.C.), 2.4 parts by weight dimorpholinodiethyl ether catalyst (available from Huntsman Corp., Houston, Tex.), 0.1 parts by weight benzoyl chloride (available from Aldrich, Milwaukee, Wis.), and 0.3 parts by weight of silicone 200 fluid (35,000 centipoise, available from Dow Corning Corp., Midland, Mich.).

The impregnated casting sheet, 3 inches by 4 yards, is rolled up into a roll.

A towelette of a rectangular (3 inches by 8 inches) piece of 100% polyester brushed tricot fabric, (weight of 2.5 ounces per square yard) is impregnated with a mixture of 98 parts by weight silicone 200 fluid (350 centistokes, available from Dow Corning Corp., Midland, Mich.) and 2 parts by weight sodium lauryl sulfate (Supralate M.E., available from Witco Corp., Houston, Tex.) in a ratio of about 2.75 grams of lubricant mixture per gram of dry fabric. The impregnated fabric is wrapped around the roll of impregnated casting sheet. The wrapped roll is sealed in a foil pouch under nitrogen.

Example 2

Preparation of a Cast Using the Lubricant-Impregnated Towelette

The sealed pouch of Example 1 is opened and the orthopedic casting article is removed. Using latex gloves, the towelette-covered roll is placed in water and squeezed twice while underwater. The roll is then taken out of the water and squeezed to remove excess amounts of water. The towelette covered roll is used to wet both gloves being worn by rolling it between the palm and wiping both palm. The towelette is then laid aside and the wrapping process begun.

The casting sheet is next unrolled while wrapping the sheet around the limb of a mannequin to form a cast. The lubricated gloves prevent the resin from the tape from sticking to the gloves and allow the hands to move freely in the molding of the cast. The towelette is used to re-apply more lubricant to coat the palms of the gloves as desired.

Example 3

Preparation of an Orthopedic Casting Kit

A towelette of a rectangular (3 inches by 8 inches) piece of 100% polyester brushed tricot fabric, (weight of 2.5 ounces per square yard) is impregnated with a slurry of 98 parts by weight silicone 200 fluid (350 centistokes, available from Dow Corning Corp., Midland, Mich.) and 2 parts by weight of 80 mesh is polyvinylpyrrolidone (PVP K120, available from ISP Technologies, Wayne, N.J.). The towelette is impregnated in a ratio of about 2.8 grams silicone slurry to about 1 gram of fabric. The impregnated fabric is wrapped around the roll of impregnated casting sheet prepared according to Example 1. The roll of casting tape has about a seven-inch circumference, providing for a half-inch overlap of the wrapped towelette. The wrapped roll is sealed in a foil pouch under nitrogen.

Example 4
Preparation of an Orthopedic Casting Kit

A substrate casting sheet of fiberglass with approximately 10% polypropylene fiber, about 3 inches wide and 4 yards long, having approximately 25% stretch, is impregnated with the following mixture: 60.18 parts by weight Isonate™ 2143L (a diphenylmethane diisocyanate resin available from Dow Chemical, Midland, Mich.), 26.43 parts by weight PPG 725 (a polypropylene glycol available from Arco Chemical Co., Charlotte, N.C.), 8.8 parts by weight P425 (WHAT IS THIS?) 2.79 parts by weight dimorpholinodiethyl ether catalyst (available from Huntsman Corp., Houston, Tex.), 0.12 parts by weight benzoyl chloride (available from Aldrich, Milwaukee, Wis.), 0.24 parts by weight of silicone 200 fluid (35,000 centipoise, available from Dow Corning Corp., Midland, Mich.), 0.24 parts by weight BHT, 0.51 parts by weight butanediol, and 0.69 parts by weight titanium dioxide.

The impregnated casting sheet, 3 inches by 4 yards, was rolled up into a roll around a low density polyethylene core 3¼ inches long. The core was formed with wall thicknesses of about 31 mils. The inner cylinder had a circular cross-section having an inner diameter of about 437 mils and an inwardly extending protuberance 60 mils long. The core had five evenly spaced L-shaped projections defining a circumference with a diameter of about 750 mils. Each projection occupied a 24° arc of the circumference. In wrapping the casting sheet, one end of the casting sheet was inserted between adjacent projections to catch when the core was spun in a clockwise rotation by the spindle.

A towelette of a rectangular (3 inches by 8 inches) piece of 100% polyester brushed tricot fabric, (weight of 2.5 ounces per square yard) laminated with a backing of low density polyethylene of 2 mils thickness before laminating was impregnated with a mixture of 98 parts by weight silicone 200 fluid (350 centistokes, available from Dow Corning Corp., Midland, Mich.) and 2 parts by weight sodium lauryl sulfate (Supralate M.E., available from Witco Corp., Houston, Tex.) in a ratio of about 2.75 grams of lubricant mixture per gram of dry fabric. The impregnated fabric was wrapped around the roll of impregnated casting sheet, with the laminated barrier layer innermost and next to the casting sheet roll. The wrapped roll was sealed in a foil pouch under nitrogen.

Example 5
Preparation of Cast Samples Using the Lubricant-Impregnated Towelette

The sealed pouch of Example 1 was opened and the orthopedic casting article was removed. Using latex gloves, the towelette-covered roll was placed in water and squeezed three times while under water with the towelette in place. The roll was then taken out of the water and squeezed to remove excess amounts of water. The towelette covered roll was used to wet both gloves being worn by rolling it between the palm and wiping both palms. The towelette was then laid aside and the wrapping process begun.

The casting sheet was next unrolled while wrapping the sheet around three 3-inch diameter cylinders on a mandrel, with one and one-third yards of the sheet being wrapped on each mandrel (about five turns of sheet per cylinder). After wrapping, the casts were molded and smoothed for one minute. The lubricated gloves prevented the resin from the tape from sticking to the gloves and allowed the hands to move freely in the molding of the cast. After the one minute of smoothing, the casts were allowed to harden. The hardening cast samples were tested at intervals of 4 minutes, 6 minutes, and 8 minutes after wrapping using a Compression Tester, Model No. 942 KVD 1000 from Compton Industries, St. Petersburg, Fla. The crush strength of the cast sample was measured using a head travel speed of 2 cm/min. The first-wrapped cylinder is tested at four minutes, the second at six minutes, and the last wrapped cylinder at eight minutes. Duplicate samples were prepared and tested for a total of nine samples measured for each time interval. The average crush strengths are shown in the table below.

Comparative Example A
Preparation of an Orthopedic Casting Kit

A comparative orthopedic casting kit was prepared using the method of Example 1, except that a core that was a smooth cylinder with a circular cross-section having an inner diameter of about 437 mils and a wall thickness of about 31 mils was substituted for the core of the invention.

Comparative Example B
Preparation of Cast Samples Using Orthopedic Casting Kit of Comparative Example A Cast samples were prepared and tested according to the procedure of Example 5. The average crush strengths are shown in the following table.

TABLE OF RESULTS

| | Average Crush Strength, lbs/3 inches | |
| --- | --- | --- |
| | Example 5 | Example B |
| 4 minutes | 10.4 | 11.4 |
| 6 minutes | 21.6 | 20.3 |
| 8 minutes | 30.3 | 26.2 |

The results show a significant increase (15.6%) in the crush strength of the casting samples when the core of the invention is used.

The invention has been described in detail with reference to preferred embodiments thereof. It should be understood, however, that variations and modifications can be made within the spirit and scope of the invention and of the following claims. In addition, while the invention has been described with particular reference to orthopedic casts and methods for forming the same, it should be understood that the inventive articles and methods described, including the methods for controlled lubricant delivery, have a broader and more general applicability, such as for molding tacky materials other than the particular casting materials described for orthopedic casts.

What is claimed is:

1. An article, comprising a roll of an orthopedic casting tape impregnated with a tacky material on a cylindrical core, wherein said core has multiple radially outwardly extending projections having an end that overhangs said core.

2. An article according to claim 1, wherein the core has up to ten projections.

3. An article according to claim 1, wherein the core has up to eight projections.

4. An article according to claim 1, wherein the core has from about three to about six projections.

5. An article according to claim 1, wherein the projections are selected from the group consisting of L-shaped projections and T-shaped projections.

6. An article according to claim 1, wherein the projections define an outer circumference having a maximum diameter of from about one-half inch to about two inches.

7. An article according to claim 1, wherein the tape comprises fibers selected from the group consisting of acrylic fibers, fiberglass, polyester fibers, polyamide fibers, polyethylene fibers, elastomeric fibers, and combinations thereof.

8. An article comprising a roll of an orthopedic casting tape impregnated with a tacky material on a cylindrical core, wherein said core has multiple radially outwardly extending projections, and further comprising a lubricant-impregnated porous substrate covering at least part of said roll.

9. An article according to claim 8, wherein the porous substrate is selected from the group consisting of films, foams, cloths, sheets, tapes, towelettes, and pads.

10. An article according to claim 8, wherein the porous substrate has a thickness of from about 0.2 mm to about 2.5 cm.

11. An article according to claim 8, further comprising a barrier layer between the lubricant-impregnated substrate and the roll.

12. An article according to claim 11, wherein the barrier layer has a thickness of from about 1 mil to about 5 mils.

13. An article according to claim 11, wherein the barrier layer is laminated on one side of the lubricant-impregnated substrate.

14. An article according to claim 8, further comprising a lubricant-impregnated porous substrate rolled together with the resin impregnated tape.

15. An article according to claim 1, wherein the core comprises a member selected from the group consisting of polyolefin materials, polyurethanes, and combinations thereof.

16. An article according to claim 1, wherein the core comprises a low density polyethylene.

17. An article according to claim 8, wherein the lubricant-impregnated porous substrate comprises a polyester material laminated on one side with a layer of a low density polyethylene.

18. An article according to claim 1, wherein the resin is a water-reactive or water-activated resin.

19. An article according to claim 18, wherein the resin is selected from the group consisting of water-reactive liquid organometallic compounds, alkoxy silane terminated polyurethane oligomers, and isocyanate-functional prepolymers.

20. An article according to claim 8, wherein the lubricant comprises at least one member selected from the group consisting of polyvinylpyrrolidone, mineral oils, water soluble or hydrophilic polymers, polyvinylpyrrolidone, and surfactants and their ionic derivatives, hydrophilic oligomeric diols, hydrophobic gels and oils, motor oils, greases, silicone fluids and silicone oils, and mixtures thereof.

21. An article according to claim 1, wherein the inner end of the rolled tape lies between adjacent projections.

22. A method of forming an orthopedic cast, comprising the steps of:

(a) immersing in water a roll of a water-reactive or water-activated resin impregnated casting material rolled on a cylindrical core, wherein said core has multiple radially outwardly extending projections having an end that overhangs said core;

(b) applying the casting material around a body member; and (c) allowing the casting material to harden to form an orthopedic cast around the body member.

23. A method according to claim 22, further including a step of squeezing the roll while the roll is immersed in the water.

24. A method according to claim 22, wherein lubricant is transferred to a gloved hand from a lubricant-impregnated porous substrate during at least one of step (a) and step (b).

25. An orthopedic casting kit comprising an article according to claim 1.

26. An orthopedic casting kit comprising an article according to claim 8.

27. An orthopedic casting kit according to claim 25, further comprising a pair of gloves.

* * * * *